United States Patent [19]

Bastart et al.

[11] Patent Number: 5,304,642

[45] Date of Patent: Apr. 19, 1994

[54] PRISTINAYMCINIA OR VIRGINIAMYCIN DERIVATIVES AND THEIR PREPARATION

[75] Inventors: Jean-Pierre Bastart, Lesigny; Jean-Marc Paris, Vaires S/Marne; Xavier Radisson, Lyon, all of France

[73] Assignee: Rhone Poulenc Sante, France

[21] Appl. No.: 908,928

[22] Filed: Jul. 2, 1992

Related U.S. Application Data

[63] Continuation of Ser. No. 629,758, Dec. 5, 1990, abandoned.

[30] Foreign Application Priority Data

Dec. 5, 1989 [FR] France .................................. 89 16030

[51] Int. Cl.$^5$ .............................................. C07D 267/00
[52] U.S. Cl. ........................................ 540/455; 540/460
[58] Field of Search ................................ 540/455, 460

[56] References Cited

U.S. PATENT DOCUMENTS

| | | | |
|---|---|---|---|
| 4,590,004 | 5/1986 | Corbet et al. | 530/317 |
| 4,617,290 | 10/1986 | Corbet et al. | 514/11 |
| 4,617,377 | 10/1986 | Corbet et al. | 530/317 |
| 4,618,599 | 10/1986 | Corbet et al. | 514/11 |

OTHER PUBLICATIONS

Fieser and Fieser, Advance Organic Chemistry, Reinhold Publishing Corporation New York, p. 463, 1961.
Corbet et al., "Chemical Abstract" vol. 103 (19), 1985 #160861e.
Corbet et al., "Chemical Abstract", vol. 103 (19), 1985 #160862f.
Corbet et al., "Chemical Abstract", vol. 103 (19), 1985 #160860d.

Primary Examiner—Nicholas S. Rizzo
Assistant Examiner—Y. N. Gupta
Attorney, Agent, or Firm—Morgan & Finnegan

[57] ABSTRACT

This invention relates to a process for preparing synergistic derivatives of formula (I), in which Y is hydrogen or dimethylamino, from pristinamycin $I_A$ or from virginiamycin, via a Mannich base, followed by elimination of the amine introduced.

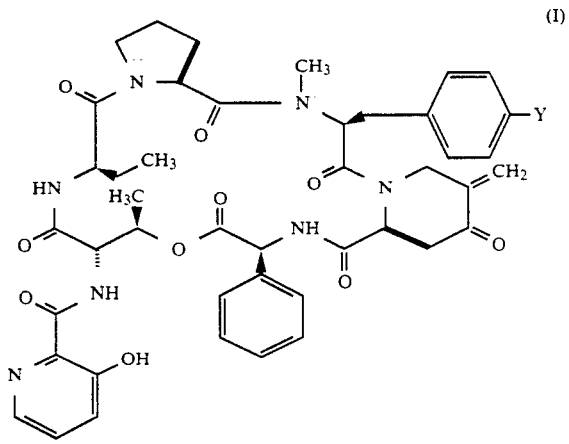

20 Claims, No Drawings

PRISTINAYMCINIA OR VIRGINIAMYCIN DERIVATIVES AND THEIR PREPARATION

This is a continuation of co-pending application Ser. No. 629,758, filed on Dec. 5, 1990 now abandoned.

FIELD OF THE INVENTION

The present invention relates to the preparation of synergistic derivatives of the general formula:

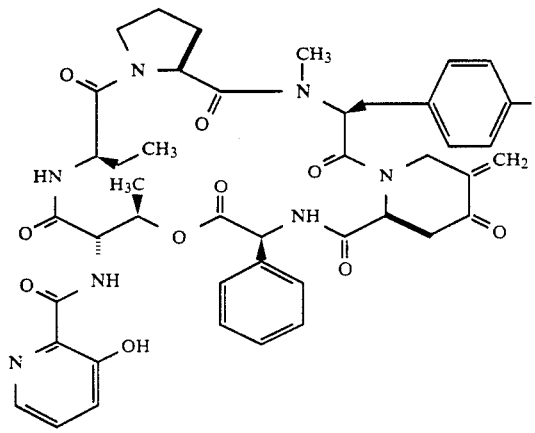

(I)

in which Y represents a hydrogen atom or a dimethylamino radical.

BACKGROUND OF THE INVENTION

The products of general formula (I) have been described as intermediates for the preparation of soluble derivatives of pristinamycin I$^4$ or of virginiamycin in European Patent Nos. 133,097 and 248,703.

According to the teaching of European Patient No. 133,097, the synergistic derivatives of general formula (I) may be obtained from natural pristinamycin I$_A$ (Y=-dimethylamino) or from virginiamycin (Y=hydrogen) of general formula (II) mentioned below, via an enamine which is treated with an alkali metal borohydride in the presence of a strong organic acid.

DESCRIPTION OF THE INVENTION

It has now been found that the synergistic derivatives of general formula (I) may be obtained from natural pristinamycin I$_A$ or from virginiamycin, proceeding via a Mannich base of general formula (III), in which Y is defined as above and R$_1$ and R$_2$ are defined as for the general formula (IV), followed by elimination of the amine introduced, according to the scheme below.

It is understood that the Mannich base of general formula (III) possesses epimeric forms, and that its epimers and the mixtures thereof fall within the scope of the present invention.

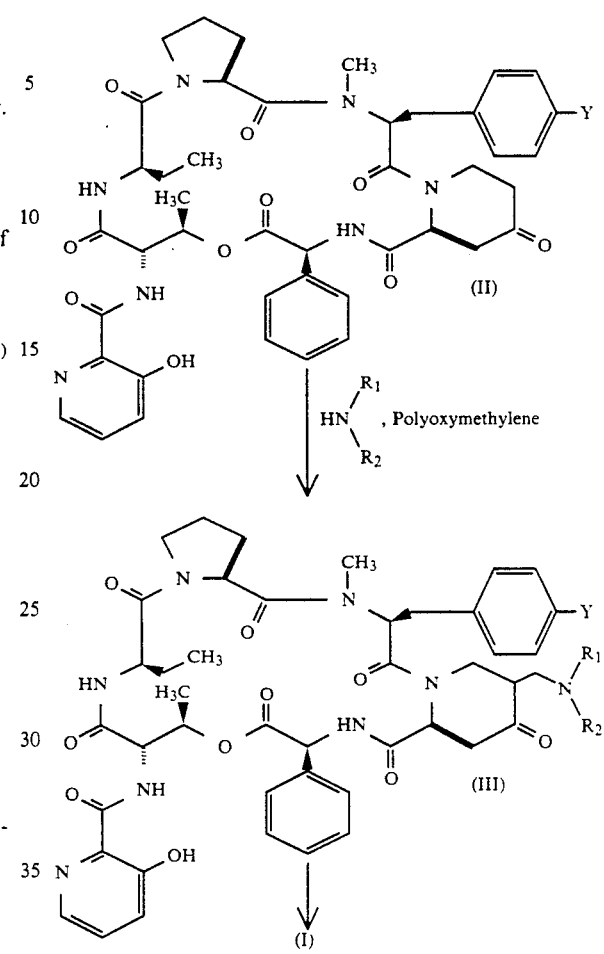

The Mannich base is prepared in the presence of an acid, by the action of polyoxymethylene and an amine of general formula:

(IV)

in which R$_1$ is a linear or branched alkyl radical containing 1 to 3 carbon atoms, R$_2$ is an alkyl radical as defined above or a phenyl radical, or alternatively R$_1$ and R$_2$, together with the nitrogen atom to which they are attached, form a saturated or unsaturated 5- or 6-membered heterocycle optionally containing another hetero atom selected from nitrogen and oxygen.

In practice, the reaction is performed at a temperature of between 20° and 50° C., in a polar protic solvent such as an alcohol (e.g. methanol, ethanol, isopropanol, polyethylene glycol) or in a polar aprotic solvent such as, e.g., dimethyl sulphoxide, and a large excess of amine (10 to 40 equivalents) and of polyoxymethylene (4 to 20 equivalents) is advantageously used, and preferably a slight excess of amine relative to the quantity of acid introduced, it being possible for the amine/acid ratio to vary from 1 to 1.3.

When the reaction is performed in the presence of an amine of general formula (I) of cyclic structure, morpholine, piperidine, pyrrolidine or imidazole is advantageously used.

The acids enabling the reaction to be catalyzed are selected from strong acids, e.g.: sulphonic acids (methanesulphonic acid, p-toluenesulphonic acid), inorganic acids (sulphuric acid, hydrochloric acid), halogenated organic acids (trifluoroacetic acid, trichloroacetic acid). It is also possible to perform the reaction in acetic acid. Another possible alternative is the use of the salt of the amine and acid employed.

Preferably, the acid will be selected in accordance with the amine employed. By way of example, when morpholine is used, the reaction is preferably performed in the presence of methanesulphonic acid or in the presence of acetic or sulphuric acid; when piperidine is used, the reaction is performed in the presence of acetic acid or para-toluenesulphonic acid; when dimethylamine is used, the reaction is preferably performed in the presence of hydrochloric acid.

The elimination of the amine is carried out in a two-phase heterogeneous phase, in a buffered acid medium, at a pH of between 3.5 and 5.

By way of example, the reaction is advantageously performed in an acetic or phosphoric acid medium.

The organic phase may be selected from solvents such as esters (e.g. ethyl acetate, isopropyl acetate), chlorinated solvents (e.g. dichloromethane) and aromatic solvents (e.g. toluene). The reaction is generally performed at a temperature of between 20° and 80° C.

EXAMPLES

The examples which follow, given without implying a limitation, illustrate the present invention.

EXAMPLE 1

A/ Mannich reaction

Methanol (120 cc), morpholine (13.8 cc; 0.157 mole; distilled over potassium hydroxide) and lastly methanesulphonic acid (8.25 cc; 0.125 mole; distilled) are introduced successively, slowly and with stirring, under argon, into a 250-cc three-necked round-bottomed flask while the temperature of the mixture is maintained at room temperature.

Pristinamycin $I_A$ ($15.7 \times 10^{-3}$ mole; 14.996 g; assay = 91% of pristinamycin $I_A$) is added in a single portion, followed by the addition of polyoxymethylene ($76.3 \times 10^{-3}$ mole; 2.294 g), and the reaction mixture heated to 40° C. with stirring for 5 hours 30 minutes. After return of the mixture to room temperature, ethyl acetate (100 cc) is added and the mixture is concentrated under reduced pressure (in a rotary evaporator) until a viscous syrup is obtained (evaporation of the MeOH/CH$_3$COOEt azeotrope). Ethyl acetate (350 cc) is added agdin, and water (350 cc), and the pH of the aqueous phase is then taken from 6.3 to 7.5 by adding saturated sodium hydrogen carbonate solution (60 cc). The phases are separated and the aqueous phase is extracted with ethyl acetate (3 × 80 cc). The combined organic phases are washed with water (3 × 100 cc) and the latter 3 aqueous phases are extracted with ethyl acetate (150 cc).

The combined organic phases are dried over sodium sulphate, filtered and concentrated in a rotary evaporator [until a solution (335 g) of crude Mannich base (5δ-(morpholinomethyl)pristinamycin $I_A$) is obtained].

B/ Elimination of the morpholine

Water (350 cc), acetic acid (18 cc; 18.88 g; 0.314 mole) and sodium acetate (1.336 g; $16.3 \times 10^{-3}$ mole) are placed successively in a 1-liter three-necked round-bottomed flask and the solution of Mannich base is then added in the course of 5 minutes (temperature rise of +2° C.). The reaction mixture is heated to +40° C. for 1 hour 50 minutes with stirring. After return of the mixture to room temperature, the pH is taken from 4 to 6.5 by adding saturated sodium hydrogen carbonate solution (250 cc) and the phases are separated. The organic phase is washed with water (3 × 100 cc) and the aqueous phases are combined and backextracted with ethyl acetate (3 × 100 cc). The organic phases are combined and treated with ethyl acetate (80 cc) in order to solubilize the product which begins to precipitate, then dried over sodium sulphate. After filtration, the solvent is evaporated off until the total mass of the solution is 116 g. The product crystallizes. After one night at +4° C., the solid is filtered off on a glass sinter (4) to yield 5δ-methylenepristinamycin $I_A$ (10.084 g) in the form of a white solid (weight yield = 72.9 %), and the filtrate is concentrated to dryness to yield a further portion (4.279 g) of 5δ-methylenepristinamycin $I_A$ (mixture of epimers) in the form of a light yellow solid (weight yield = 30.9%).

HPLC assay

- Crystals: 10.08 g
  Assay of 5δ-methylenepristinamycin $I_A$: 93.5%
  True yield: 68%
- Concentrate of the mother liquors: 4.28 g
  Assay of 5δ-methylenepristinamycin $I_A$: 33%
  True yield : 10%

Equivalent to a total true yield = 78% of 5δ-methylenepristinamycin $I_A$.

EXAMPLE 2

A/Mannich reaction

Methanol (10 cc), morpholine (0.846 cc; $9.7 \times 10^{-3}$ mole, distilled over potassium hydroxide) and lastly p-toluenesulphonic acid (1.476 g; $7.76 \times 10^{-3}$ mole) are introduced successively, slowly and with stirring, under argon, into a 25-cc round-bottomed flask while the temperature of the mixture is maintained at 45° C.

Pristinamycin $I_A$ (1 g; $0.97 \times 10^{-3}$ mole; assay = 84% of pristinamycin $I_A$) is added in a single portion. The reaction mixture is treated with polyoxymethylene (0.140 g; $5 \times 10^{-}$mole) and then heated to 50° C. with stirring for 7 hours 45 minutes. After return of the mixture to room temperature, ethyl acetate (10 cc) is added and the mixture is concentrated under reduced pressure (in a rotary evaporator) until a viscous syrup is obtained (evaporation of the MeOH/CH$_3$COOEt azeotrope). Ethyl acetate (30 cc) is added again, and water (10 cc).

The aqueous and organic phases are separated and the aqueous phase is extracted with ethyl acetate (1 × 10 cc). The combined organic phases are washed with water (3 × 10 cc) and then concentrated in a rotary evaporator [until a solution (approximately 25 g) of crude Mannich base (5δ-(morpholinomethyl)pristinamycin $I_A$ - (mixture of epimers) is obtained].

B/ Elimination of the morpholine

Water (25 cc), acetic acid (0.838 cc) sodium acetate (0.082 g) are placed successively in a 100-cc round-bottomed flask and the solution of Mannich base is added in a single portion. The reaction mixture is heated to +50° C. for 1 hour with stirring. After return of the mixture to room temperature, the aqueous phase is separated off and back-extracted with ethyl acetate (15 cc) and the combined organic phases are treated with water (20 cc). The pH is adjusted to neutrality by adding sodium hydroxide solution (1N) and the organic phase is separated, washed with water (2×10 cc) and brine (1×10 cc) and then dried over sodium sulphate. After filtration, the solvent is evaporated off to obtain a dry product (900 mg) assaying at 77.5%, equivalent to an 81% yield. This product could be recrystallized to yield the usual grade with an 80% recrystallization yield.

EXAMPLE 3

Mannich reaction -
5δ-(morpholinomethyl)pristinamycin $I^A$ (mixture of epimers).

Methanol (1 cc) and morpholine methanesulphonate (421.4 mg; $2.30 \times 10^{-3}$ mole) are introduced successively, slowly and with stirring, under argon, into a 15-cc three-necked round-bottomed flask. Pristinamycin $I_A$ (100 mg; $0.115 \times 10^{-3}$ mole) is added in a single portion, followed by the addition of polyoxymethylene (69 mg; $2.31 \times 10^{-3}$ mole), and the reaction mixture is stirred at 28° C. for 24 hours. An HPLC assay of the crude reaction product enables an estimate of the yield to be made.

Degree of conversion: 98%

True yield: 70%

The elimination of the morpholine may be performed under the conditions described above in Example 1 or Example 2.

EXAMPLE 4

Mannich reaction -
5δ-(morpholinomethyl)pristinamycin $I_A$ (mixture of epimers).

Methanol (3.2 cc), morpholine (0.368 cc; $4.187 \times 10^{-3}$ mole; distilled over potassium hydroxide) and lastly sulphuric acid (0.223 cc; $4.187 \times 10^{-3}$ mole; distilled) are introduced successively, slowly and with stirring, under argon, into a 15-cc three-necked round-bottomed flask while the temperature of the mixture is maintained at room temperature. Pristinamycin $I_A$ (0.1 g; $0.105 \times 10^{-3}$ mole; assay=91% of pristinamycin $I_A$) is added in a single portion, followed by the addition of polyoxymethylene (69 mg; $2.31 \times 10^{-3}$ mole), and the reaction mixture is stirred at 25° C. for 48 hours.

An HPLC assay of the crude reaction product enables an estimate of the yield to be made.

Degree of conversion: 99%

True yield: 80%

The elimination of the morpholine may be performed as described above in Example 1 or Example 2.

EXAMPLE 5

Mannich reaction -
5δ-(morpholinomethyl)pristinamycin $I_A$ (mixture of epimers).

Methanol (3.2 cc), morpholine (0.368 cc; $4.187 \times 10^{-3}$ mole; distilled over potassium hydroxide) and lastly acetic acid (0.251 g; $4.187 \times 10^{-3}$ mole) are introduced successively, slowly and with stirring, under argon, into a 15-cc three-necked round-bottomed flask while the temperature of the mixture is maintained at room temperature. Pristinamycin $I_A$ (0.1 g; $0.105 \times 10^{-3}$ mole; assay=91% of pristinamycin $I_A$) is added in a single portion, followed by the addition of polyoxymethylene (69 mg; $2.31 \times 10^{-3}$ mole), and the reaction mixture is stirred at 25° C. for 24 hours.

HPLC assay of the crude reaction product enables an estimate of the yield to be made.

Degree of conversion: 98%

True yield: 70%

The elimination of the morpholine may be performed as described above in Example 1 or Example 2.

EXAMPLE 6

Dimethylamine hydrochloride (81.5 g), polyoxymethylene (30 g) and pristinamycin $I_A$ (43.3 g) are added with stirring to methanol (430 cc) heated to 45° C. The suspension obtained is then stirred for 10 hours at 45° C. The reaction mixture is then filtered and the cake is washed with methanol (2×25 cc). Ethyl acetate (900 cc) is added to the combined filtrate; the pH of the aqueous phase is brought to 7 by adding saturated sodium hydrogen carbonate solution (65 cc).

The organic phase is separated off after settling has taken place; the aqueous phase is extracted with ethyl acetate (200 cc) and the combined organic phases are then washed with a mixture of water (500 cc) and saturated sodium chloride solution off (50 cc). The aforementioned organic phase containing 5δ-(dimethylaminomethyl)pristinamycin $I_A$ is then poured into a stirred solution, maintained at 35° C., of acetic acid (43.3 cc) and sodium acetate (4.3 g) in water (1000 cc). The reaction mixture is stirred and heated to 35° C. for 1 hour. The organic phase is then separated off after settling has taken place, washed twice with a mixture of water (500 cc) and saturated sodium chloride solution (50 cc) and then, after the addition of methylene chloride (180 cc), washed with saturated sodium hydrogen carbonate solution (195 cc). The organic phase is again washed twice with a mixture of water (500 cc) and saturated sodium chloride solution (50 cc), then dried over sodium sulphate, filtered and concentrated under reduced pressure (2.7 kPa) at 30° C. The solid obtained is then stirred for 1 hour at a temperature in the region of 20° C. in ethyl ether (400 cc). The suspension obtained is filtered on a glass sinter; after drying in the air overnight at a temperature in the region of 20° C., 5δ-methylenepristinamycin $I_A$ (36.4 g) is obtained in the form of a white powder, m.p. about 230° C. The assay of this product is 77.6% (HPLC).

EXAMPLE 7

A/ Mannich reaction

A 250-cc three-necked round-bottomed flask is charged successively under nitrogen with methanol (150 cc), morpholine (13.8 cc; 0.157 mole), then, in the course of 10 minutes, methanesulphonic acid (8.3 cc; 0.126 mole), and finally polyoxymethylene (2.3707 g; 0.0785 mole) and pristinamycin $I_A$ (17.0055 g; assay=80.5%; equivalent to $15.78 \times 10^{-3}$ mole). The reaction mixture is stirred for 5 hours 25 minutes at 40°–43° C. and then filtered on kieselguhr after return of the mixture to room temperature. The filtrate is concentrated under reduced pressure to a weight of 75.30 g and then treated with water (35 cc), ethyl acetate (250 cc) and water (100 cc). The organic phase is separated off after settling has taken place and washed with water (3×50 cc). The aqueous phases are combined and backextracted with ethyl acetate (3×20 cc). These back-extraction solutions are combined and washed with water (20 cc). The organic phases are combined, dried over sodium sulphate and concentrated to dryness under reduced pressure to obtain a crude product (19.21 g). A portion (10.3405 g) of this crude product is stirred vigorously in water (150 cc) at room temperature for 3 hours 30 minutes and then filtered on a glass sinter. The solid is washed with water (3×20 cc) and then dried to obtain a mixture (8.9397 g) of the two epimers of 5δ-(morpholinomethyl)pristinamycin $I_A$. $^{13}C$ NMR CDCl$_3$, 90 MHz, HMDS (reference), δ in ppm (numbering indicated according to the recommendation of J. O. Anteunis et al., Eur. J. Biochem., 58, 259 (1975) and mentioned in European Patent Application No. 133,037).

| Preponderant epimer: | |
| --- | --- |
| 71.95 | (d; 1x) |
| 67.00 | (t; —CH$_2$-morpholine) |
| 57.6 | (d; 3α) |
| 57.3 | (d; 5α) |
| 56.1 | (d; 1α + 6α) |
| 55.4; 55.1 | (t; 5ε + —CH$_2$—N⟋  at position 5δ) |
| 53.9 | (d; 4α) |
| 53.6 | (t; —CH$_2$-morpholine) |
| 51.4 | (d; 2α) |
| 47.8 | (t; 3δ) |
| 45.4 | (d; 5δ) |
| 41.4 | (t; 5x) |
| 40.6 | (q; —N(CH$_3$)$_2$) |
| 35.6 | (t; 4x) |
| 31.0 | (q; ⟍N—CH$_3$) |
| 27.7 | (t; 3x) |
| 25.1 | (t; 2x) |
| 24.6 | (t; 3x) |
| 16.6 | (q; 1x) |
| 10.0 | (q; 2x) |

B/ Elimination of morpholine

A solution in ethyl acetate (75 cc) of the Mannich base prepared above (3.9989 g, corresponding to approximately $3.72 \times 10^{-3}$ mole) is added to a solution of acetic acid (4.25 cc; $74.2 \times 10^{-3}$ mole) and sodium acetate (312.7 mg; $3.76 \times 10^{-3}$ mole) in water (75 cc). The mixture is stirred at 41°–44° C. for 4 hours 40 minutes. The reaction is complete in 1 hour. After return of the mixture to room temperature, the pH is taken from 3.9 to 7 by adding sodium bicarbonate (60 cc, saturated aqueous solution). The aqueous phase is separated off and washed with ethyl acetate (20 cc), and the organic phases are combined, washed with water (3×20 cc) and then dried over sodium sulphate. After concentration to dryness under reduced pressure, 5δ-methylenepristinamycin $I_A$ (3.4419 g; assay=70%) is obtained in the form of a white solid, with an overall yield of 72% from pristinamycin $I_A$.

EXAMPLE 8

Mannich reaction -
5δ-(morpholinomethyl)pristinamycin $I_A$ (mixture of epimers).

2-Propanol (5 cc), morpholine (0.40 cc; $4.57 \times 10^{-3}$ mole), methanesulphonic acid (0.24 cc; $3.64 \times 10^{-3}$ mole), polyoxymethylene (70.0 mg; $2.32 \times 10^{-3}$ mole) and pristinamycin $I_A$ (501 mg; assaying at 80.5%; equivalent to $4.65 \times 10^{-4}$ mole) are introduced successively into a 25-cc three-necked round-bottomed flask. The reaction mixture is stirred for 9 hours 40 minutes at 43°–45° C. An HPLC chromatogram of this reaction mixture then makes it possible to estimate a degree of conversion: DC=92%; and a yield of converted product: CY=75%.

The elimination of the morpholine may be performed under the conditions described in the previous examples or in Example 9.

EXAMPLE 9

A/ Mannich reaction

Ethanol (5 cc), morpholine (0.40 cc; $4.57 \times 10^{-3}$ mole), methanesulphonic acid (0.24 cc; $3.64 \times 10^{-3}$ mole), polyoxymethylene (69.5 mg; $2.31 \times 10^{-3}$ mole) and pristinamycin $I_A$ (498.6 mg; assaying at 80.5%; equivalent to $4.63 \times 10-4$ mole) are introduced successively into a 25-cc three-necked round-bottomed flask. The reaction mixture is stirred for 5 hours 15 minutes at 40°–45° C. After return of the mixture to room temperature and the addition of toluene (25 cc) and water (25 cc), the pH is taken from 6 to 7 by adding saturated sodium bicarbonate solution. The aqueous phase is separated off after settling has taken place and washed with toluene (3×10 cc). The organic phases containing 5δ-(morpholinomethyl)pristinamycin $I_A$ (mixture of epimers) are combined and washed with water (3×10 cc).

B/ Elimination of the morpholine

The toluene solution of crude Mannich bases obtained above is poured in a single portion into a solution of acetic acid (0.53 cc; $9.26 \times 10-3$ mole) and sodium acetate (41.4 mg; $4.98 \times 10-4$ mole) in water (50 cc). This two-phase mixture is stirred at 45°–47° C. for 3 hours 30 minutes. After return of the mixture to room temperature, the pH is taken from 4.7 to 7 by adding saturated aqueous sodium bicarbonate solution. The aqueous phase is separated off after settling has taken place and washed with toluene (2×10 cc). The organic phases are combined and washed with water (2×25 cc). After drying, the toluene solution is concentrated to dryness under reduced pressure to obtain 5δ-methylenepristinamycin $I_A$ in a 62% yield (assayed by HPLC).

EXAMPLE 10

Mannich reaction -
5δ-(morpholinomethyl)pristinamycin $I_A$ (mixture of epimers).

Dimethyl sulphoxide (5 cc), morpholine (0.40 cc; $4.57 \times 10^{-3}$ mole), methanesulphonic acid (0.24 cc; $3.64 \times 10^{-3}$ mole), pristinamycin $I_A$ (498 mg; assay 80.5%; equivalent to $4.62 \times 10^{-4}$ mole) and polyoxymethylene (72.7 mg; $2.42 \times 10^{-3}$ mole) are introduced successively into a 25-cc round-bottomed flask. The reaction mixture is stirred for 4 hours 45 minutes at 43°–46° C. An HPLC assay makes it possible to estimate the degree of conversion: DC=97% and the yield of useful products (Mannich base containing, in addition, 5δ-methylenepristinamycin I$_A$) relative to the product converted: CY=70%. The elimination of the morpholine may be performed as described above.

EXAMPLE 11

Mannich reaction -
5δ-(morpholinomethyl)pristinamycin I$_A$ (mixture of epimers).

Ethylene glycol (5 cc), morpholine (0.40 cc; $4.57 \times 10^{-3}$ mole), methanesulphonic acid (0.24 cc; $3.64 \times 10^{-3}$ mole), polyoxymethylene (69.9 mg; $2.32 \times 10^{-3}$ mole) and pristinamycin A (506.8 mg; assay =80.5%; equivalent to $4.7 \times 10^{-4}$ mole) are introduced successively into a 25-cc round-bottomed flask. The reaction mixture is stirred for 1 hour at approximately 45° C. An HPLC assay makes it possible to estimate the degree of conversion: DC=95%; and the yield of useful products (Mannich base containing, in addition, 5δ-methylenepristinamycin I$_A$) relative to the pristinamycin I$_A$ converted: CY=65%.

EXAMPLE 12

A/ Mannich reaction

Methanol (14 cc), morpholine (1.50 cc; $17.1 \times 10^{-3}$ mole), methanesulphonic acid (0.90 cc; $13.6 \times 10^{-3}$ mole), virginiamycin S, (1.4032 g; $1.70 \times 10^{-3}$ mole) and polyoxymethylene (253 mg; $8.4 \times 10^{-3}$ mole) are introduced successively into a 25-cc three-necked round-bottomed flask. After stirring for 3 hours 30 minutes at 45° C., the temperature is taken to approximately 20° C. and the methanol is evaporated off under reduced pressure. The crude residue is taken up with ethyl acetate (30 cc) and water (30 cc). The pH is taken from 6 to 7 by adding saturated aqueous sodium bicarbonate solution, and the aqueous phase is separated off after settling has taken place and washed with ethyl acetate (3×10 cc). The organic phases containing 5δ-(morpholinomethyl)virginiamycin S$_1$ (mixture of epimers) are combined and washed with water (3×10 cc).

B/ Elimination of morpholine

In a 250-cc round-bottomed flask, the organic solution of Mannich base obtained above is poured into a solution of acetic acid (1.95 cc; $34 \times 10^{-3}$ mole) and sodium acetate (149 mg; $1.79 \times 10^{-3}$ mole) in water (50 cc). The two-phase mixture is stirred at 46° C. for 3 hours. After return of the mixture to room temperature, the pH of the aqueous phase is taken from 4.05 to 6.7 by adding saturated sodium bicarbonate solution. The aqueous phase is separated off after settling has taken place and washed with ethyl acetate (3×10 cc), the organic phases are combined and the combined phases are washed with water (3×10 cc). After drying over sodium sulphate and filtration, the organic solution is concentrated to 15.3 g and 5δ-methylenevirginiamycin S$_1$ crystallizes overnight at +4° C. After filtration, a pure product (581.5 mg) is thereby obtained (the mother liquors may be concentrated to yield a second crop of crystallized product of good purity).

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

What is claimed is:

1. A derivative of formula:

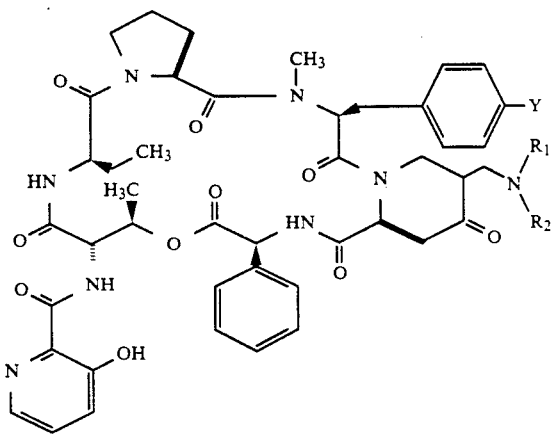

in which R$_1$, R$_2$ and Y are defined in its epimeric forms or the mixtures thereof.

2. A process for preparing derivatives of formula:

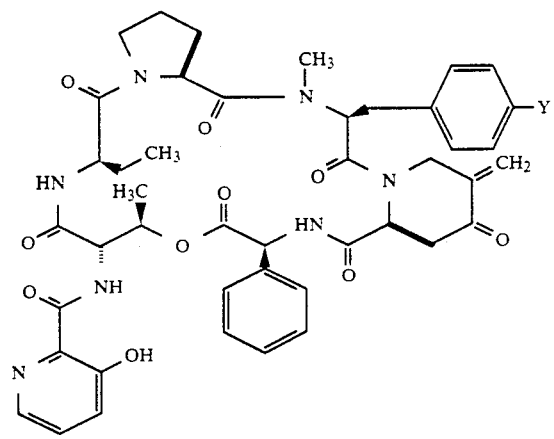

in which Y represents a hydrogen atom or a dimethylamino radical, wherein a Mannich base of formula:

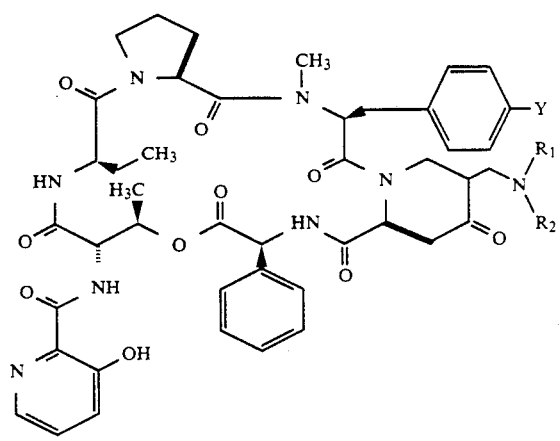

in which Y is defined as above and $R_1$ represents a linear or branched alkyl radical containing 1 to 3 carbon atoms, $R_2$ is an alkyl radical as defined above or a phenyl radical, or alternatively $R_1$ and $R_2$, together with the nitrogen atom to which they are attached, form a saturated or unsaturated 5- or 6-membered heterocycle optionally containing another hetero atom selected from nitrogen and oxygen, is prepared in the presence of an acid, by the action of polyoxymethylene and an amine of formula:

in which $R_1$ and $R_2$ are as above defined, on pristinamycin $I_A$ or virginiamycin, and the amine introduced is then eliminated.

3. A process according to claim 2, wherein the action of polyoxymethylene and the amine on pristinamycin $I_A$ or virginiamycin is conducted at a temperature of between about 20° C. to 50° C. in a polar solvent.

4. A process according to claim 3, wherein the polar solvent is a polar protic solvent selected from the group consisting of methanol, ethanol, isopropanol, or polyethylene glycol.

5. A process according to claim 3, wherein the polar solvent is a polar aprotic solvent such as dimethyl sulfoxide.

6. A process according to claim 2, wherein the amine substituent is selected from the group consisting of morpholine, piperidine, pyrrolidine, or imidazole.

7. A process according to claim 2, wherein said acid is a strong acid selected from the group consisting of sulphonic acids, inorganic acids, or halogenated organic acids.

8. A process according to claim 7, wherein the acid is selected from the group consisting of methane sulphonic acid, p-toluenesulphonic acid, sulphuric acid, hydrochloric acid, trifluoroacetic acid, or trichloroacetic acid.

9. A process according to claim 2, wherein the amine to acid ratio varies from between 1 to about 1.3.

10. A process according to claim 2, wherein the elimination of the amine substituent is conducted at a pH of between about 3.5 and 5.

11. A process according to claim 2, wherein the elimination of the amine substituent is performed in the presence of an acetic or phosphoric acid medium.

12. A process according to claim 2, wherein the elimination reaction is performed at a temperature of between about 20° C. to about 80° C.

13. A process according to claim 2 for preparing 5δ-methylenepristinamycin $I_A$, comprising contacting pristinamycin $I_A$ with morpholine in the presence of polyoxymethylene, methanol, methane sulphonic acid and ethylacetate, at elevated temperature, to produce 5δ-(morpholinomethyl)pristinamycin $I_A$, and subsequently eliminating the morpholine group to produce 5δ-methylenepristinamycin $I_A$.

14. A process according to claim 2 for preparing 5δ-methylenepristinamycin $I_A$, comprising contacting pristinamycin $I_A$ with morpholine in the presence of polyoxymethylene, methanol, and p-toluenesulphonic acid and ethylacetate, at elevated temperature, to produce 5δ-(morpholinomethyl)pristinamycin $I_A$, and subsequently eliminating the morpholine group to produce 5δ-methylenepristinamycin $I_A$.

15. A process according to claim 2 for preparing 5δ-methylenepristinamycin $I_A$, comprising contacting pristinamycin $I_A$ with dimethylamine hydrochloride in the presence of polyoxymethylene, methanol and ethylacetate, at elevated temperature, to produce 5δ-(morpholinomethyl)pristinamycin $I_A$, and subsequently eliminating the dimethylamine group to produce 5δ-methylene-pristinamycin $I_A$.

16. A process according to claim 2 for preparing 5δ-methylenepristinamycin $I_A$, comprising contacting virginamycin $S_1$ with morpholine in the presence of polyoxymethylene, methanol, methane sulphonic acid and ethylacetate, at elevated temperature to produce 5δ-(morpholinomethyl)pristinamycin $I_A$, and subsequently eliminating the morpholine group to produce 5δ-methylenepristinamycin $I_A$.

17. A process for preparing 5δ-(morpholinomethyl) pristinamycin $I_A$ epimers comprising, forming a mixture of pristinamycin $I_A$, 2-propanol, morpholine, methane sulphonic acid and polyoxymethylene, and reacting the mixture at elevated temperature to produce the 5δ-(morpholinomethyl)pristinamycin $I_A$ epimers.

18. A process for preparing 5δ-(morpholinomethyl) pristinamycin $I_A$ epimers comprising, forming a mixture of pristinamycin $I_A$, polyoxymethylene, ethanol, morpholine, methane sulphonic acid and reacting the mixture at elevated temperature to produce the 5δ-(morpholinomethyl)pristinamycin $I_A$ epimers.

19. A process for preparing 5δ-(morpholinomethyl) pristinamycin $I_A$ epimers comprising, forming a mixture of pristinamycin $I_A$, polyoxymethylene, dimethylsulphoxide, morpholine, and methane sulfonic acid, and reacting the mixture at elevated temperature to produce the 5δ-(morpholinomethyl) pristinamycin $I_A$ epimers.

20. The process for preparing 5δ-(morpholinomethyl) pristinamycin $I_A$ epimers comprising, forming a mixture of pristinamycin $I_A$, polyoxymethylene, ethylene glycol, morpholine, methane sulfonic acid, and reacting the mixture at elevated temperature to produce the 5δ-(morpholinomethyl)pristinamycin $I_A$ epimers.

* * * * *